(12) United States Patent
Marseille et al.

(10) Patent No.: US 9,125,978 B2
(45) Date of Patent: *Sep. 8, 2015

(54) CANNULA FOR HEART CHAMBER IMPLANTATION AND RELATED SYSTEMS AND METHODS

(71) Applicant: CircuLite, Inc., Teaneck, NJ (US)

(72) Inventors: Oliver Marseille, Aachen (DE); Walid Aboulhosn, Btekhnay (LB)

(73) Assignee: CircuLite, Inc., Teaneck, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,334

(22) Filed: Aug. 23, 2013

(65) Prior Publication Data

US 2013/0338426 A1 Dec. 19, 2013

Related U.S. Application Data

(62) Division of application No. 12/144,738, filed on Jun. 24, 2008, now Pat. No. 8,545,379.

(60) Provisional application No. 60/950,702, filed on Jul. 19, 2007.

(51) Int. Cl.
*A61M 1/12* (2006.01)
*A61M 1/10* (2006.01)
(Continued)

(52) U.S. Cl.
CPC .............. *A61M 1/12* (2013.01); *A61B 17/3421* (2013.01); *A61M 25/008* (2013.01);
(Continued)

(58) Field of Classification Search
CPC ......... A61M 1/122; A61M 1/12; A61M 1/10; A61M 1/3659; A61M 1/3653; A61M 1/1008

USPC ....................... 600/16, 17; 607/130; 623/3.26
See application file for complete search history.

(56) References Cited

U.S. PATENT DOCUMENTS 3,903,895 A * 9/1975 Alley et al. .................. 604/178
6,585,767 B1 * 7/2003 Holley et al. ................ 623/2.41
(Continued)

FOREIGN PATENT DOCUMENTS

CA 2300881 A1 2/1999
CA 2414225 A1 12/2001
(Continued)

OTHER PUBLICATIONS

Japanese Patent Office, Notice of Reasons for Rejection in JP Application No. 2010-517041, Feb. 10, 2014.
(Continued)

*Primary Examiner* — William Levicky
(74) *Attorney, Agent, or Firm* — Wood, Herron & Evans, LLP

(57) ABSTRACT

A cannula for implantation into a chamber of a heart includes an elongate body having a lumen extending along a longitudinal axis, a first end, and a second end. The first and second ends define openings into the lumen and the second end includes a flat portion. A flared tip portion extends from the flat portion of the second end in a direction toward the first end, and flares radially outward from the longitudinal axis and in such direction. A ring member extends around the axis of the elongate body and is spaced from the flared tip portion, and the ring member is adapted for retaining the elongate body in a position relative to a wall of the chamber. An embodiment of a flared tip portion may further include a barbed surface configured to contact tissue around an aperture in the wall of the heart when the cannula travels through the aperture.

11 Claims, 8 Drawing Sheets

(51) Int. Cl.
*A61M 1/36* (2006.01)
*A61B 17/34* (2006.01)
*A61M 25/00* (2006.01)
*A61M 25/04* (2006.01)
*A61B 17/00* (2006.01)

(52) U.S. Cl.
CPC ...... *A61M 25/0068* (2013.01); *A61M 25/0074* (2013.01); *A61M 25/04* (2013.01); *A61B 2017/00252* (2013.01); *A61B 2017/3425* (2013.01); *A61B 2017/3488* (2013.01); *A61M 1/1008* (2014.02)

(56) References Cited

U.S. PATENT DOCUMENTS 7,918,800 B1 * 4/2011 Brown et al. ................ 600/481
2002/0082467 A1 * 6/2002 Campbell ...................... 600/16
2006/0184088 A1 * 8/2006 Van Bibber et al. ............. 604/8
2008/0004485 A1 * 1/2008 Moreschi ........................ 600/16
2008/0076960 A1 * 3/2008 Marseille et al. ............... 600/16

FOREIGN PATENT DOCUMENTS

| JP | 59103667 | 6/1984 |
| JP | 62202847 | 12/1987 |
| JP | 286553 | 7/1990 |

OTHER PUBLICATIONS

Canadian Patent Office, Office Action in CA Application No. 2,693,223, Apr. 29, 2014.

* cited by examiner

CANNULA FOR HEART CHAMBER IMPLANTATION AND RELATED SYSTEMS AND METHODS

CROSS-REFERENCE TO RELATED APPLICATION

This application is a divisional of U.S. application Ser. No. 12/144,738, filed Jun. 24, 2008 (now U.S. Pat. No. 8,545,379) which claims the benefit of U.S. Provisional Patent Application Ser. No. 60/950,702, filed on Jul. 19, 2007, the disclosures of which are incorporated by reference herein.

TECHNICAL FIELD

This invention generally relates to cannulae and, more particularly, for example, to cannulae for implantation into fluid communication with a chamber of a human heart.

BACKGROUND

Guided flow of blood into or out of a chamber of a human heart is sometimes necessary. For example, it may be desirable to guide or direct blood from a ventricle and into a ventricle assist device that aids the heart in delivering blood to the body. Similarly, it may be desirable to guide or direct blood to or from other locations, such as from a device and into an atrium of the heart.

To that end, devices such as cannulae are known that guide blood into or out of the heart. Such devices may be designed to be inserted into a chamber of a heart through an aperture in a wall of the chamber of the heart.

SUMMARY

In accordance with one set of embodiments, a cannula for implantation into a chamber of a heart includes an elongate body having a lumen extending along a longitudinal axis, a first end, and a second end. The first and second ends define openings into the lumen and the second end includes a flat portion. A flared tip portion extends from the flat portion of the second end in a direction toward the first end, and flares radially outward from the longitudinal axis and in such direction. A first ring member extends around the axis of the elongate body and is spaced from the flared tip portion, and the first ring member is adapted for retaining the elongate body in a position relative to a wall of the chamber.

In one aspect of this set of embodiments, the flared tip portion may further include a barbed surface configured to contact tissue around an aperture in the wall of the chamber of the heart when the elongate body travels through the aperture.

The first ring member and/or flared tip portion may include a resilient material such as silicone. Likewise, the first ring member may include a fabric adapted to be sutured to a wall of the heart. The fabric may alternatively or additionally be adapted for tissue ingrowth therethrough. The flared tip portion may include a rigid material. For example, the material may include a metal such as titanium. Alternatively or in addition, the flared tip portion may include a resilient material such that, for example, at least a portion of the flared tip portion may flex toward the longitudinal axis when the elongate body travels through the aperture in the wall of the heart. The cannula may also include a second ring member that is spaced from the first ring member and which includes a fabric that is adapted to be sutured to the wall of the heart. The fabric may alternatively or additionally be adapted for tissue ingrowth therethrough.

In another embodiment, a method of implanting a cannula into a chamber of a heart includes moving the cannula in a first direction through an aperture into the chamber. The chamber receives a flared tip portion of the cannula extending from a flat portion thereof. A position of the cannula within the chamber is established by contacting a wall of the chamber with a ring member extending around a longitudinal axis of the cannula.

In yet another embodiment, a heart assist system for coupling into fluid communication with a chamber of a heart includes a blood pump including an inlet and a cannula with one or more of the features, alone or in combination, generally described above for the respective cannulae of the different embodiments.

BRIEF DESCRIPTION OF THE DRAWINGS

Various additional features and aspects will become readily apparent to those of ordinary skill in the art from the following description of illustrative embodiments of the invention and from the drawings in which.

DETAILED DESCRIPTION

Figure 1:
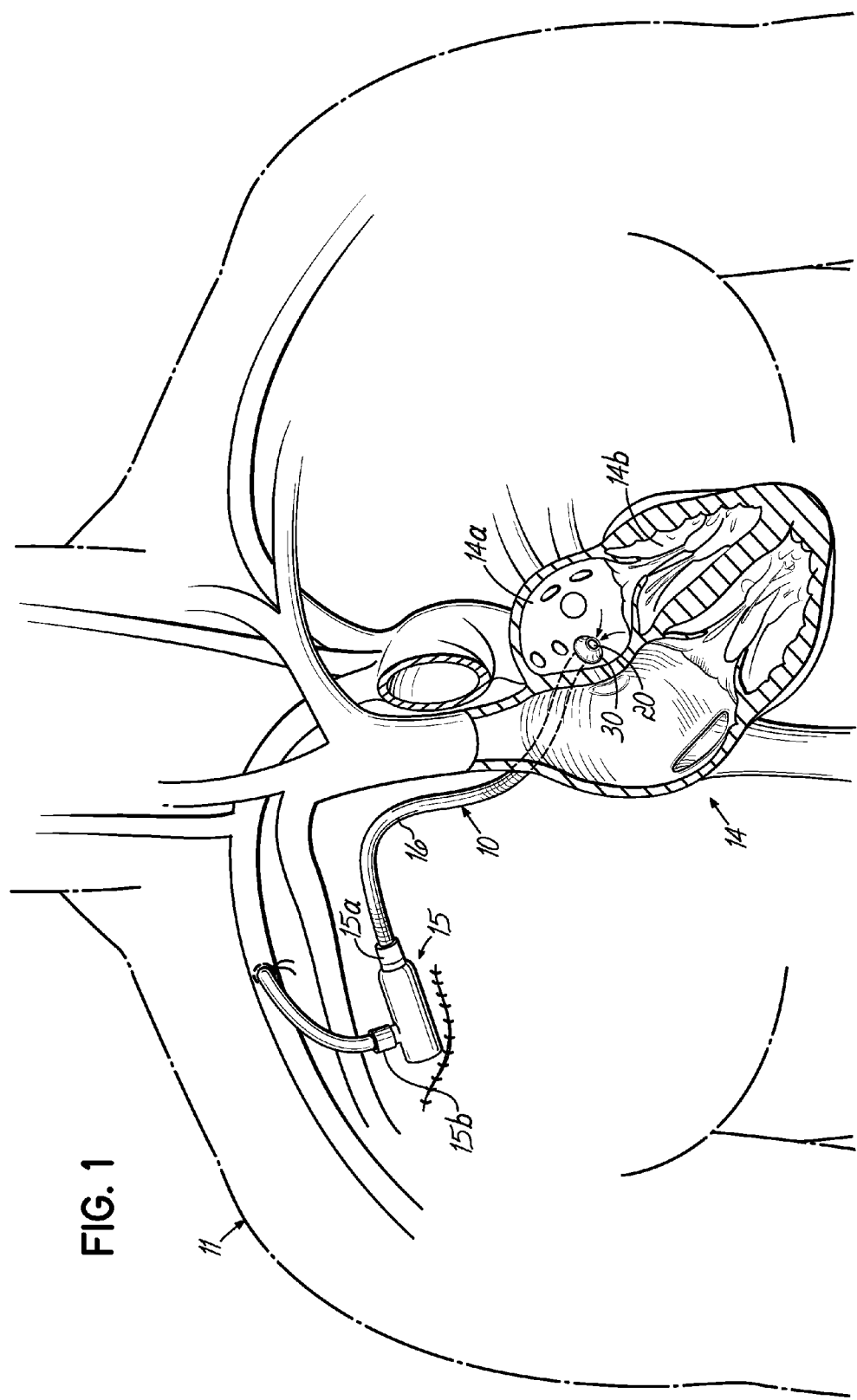
FIG. 1 is a partial cross-sectional view of a heart in a human body, depicting an exemplary use of a cannula as part of a heart assist system.
Figure 2A:
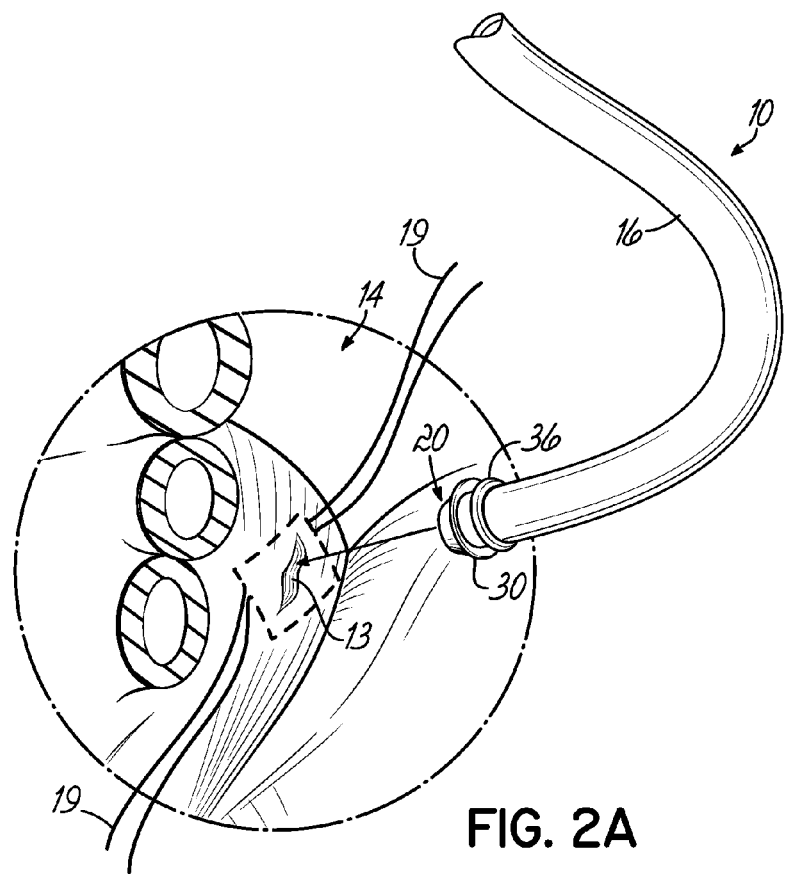
FIG. 2A is a perspective view of an exemplary cannula prior to implantation in a human heart.
Figure 2B:
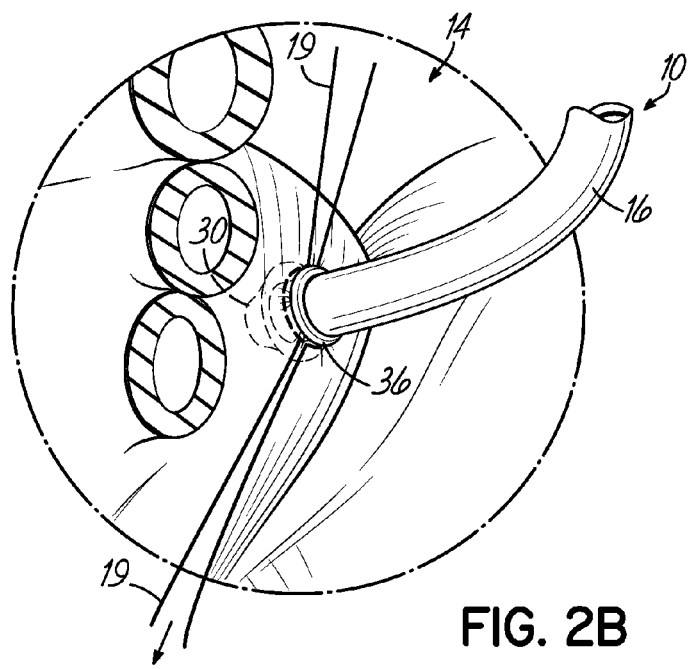
FIG. 2B is a perspective view of the cannula of FIG. 2A depicting a subsequent step in the implantation thereof.

With reference to the figures and, more particularly to FIGS. 1 and 2A-2B, a cannula 10 is adapted for implantation into a chamber of a heart 14. Such chamber may, for example, be one on the left side of the heart 14 such as a left atrium 14a or a left ventricle 14b. Implantation may be carried out, for example, by inserting a portion of the cannula 10 into the chamber 14a through an incision or aperture 13 communicating an interior of the chamber 14a with an exterior thereof.

Once implanted, the cannula 10 may permit flow of blood between the chamber 14a and other locations of the human body 11 or devices such as a heart-assist device or blood pump 15. For example, the blood pump 15 may be of the type disclosed in U.S. Pat. No. 6,116,862, the disclosure of which is fully incorporated by reference herein. The cannula 10 may thus be coupled into fluid communication with the chamber 14a and further into fluid communication with an inlet 15a of the blood pump 15. Another cannula may also be connected into fluid communication with an outlet 15b of the blood pump 15 and, ultimately, to the circulatory system of the patient, as shown for example in FIG. 1. Moreover, fixation of the cannula 10 in the chamber 14a may include the application of sutures 19 or the like through or about portions of the cannula 10 and through surfaces of the heart 14.

Figure 3:
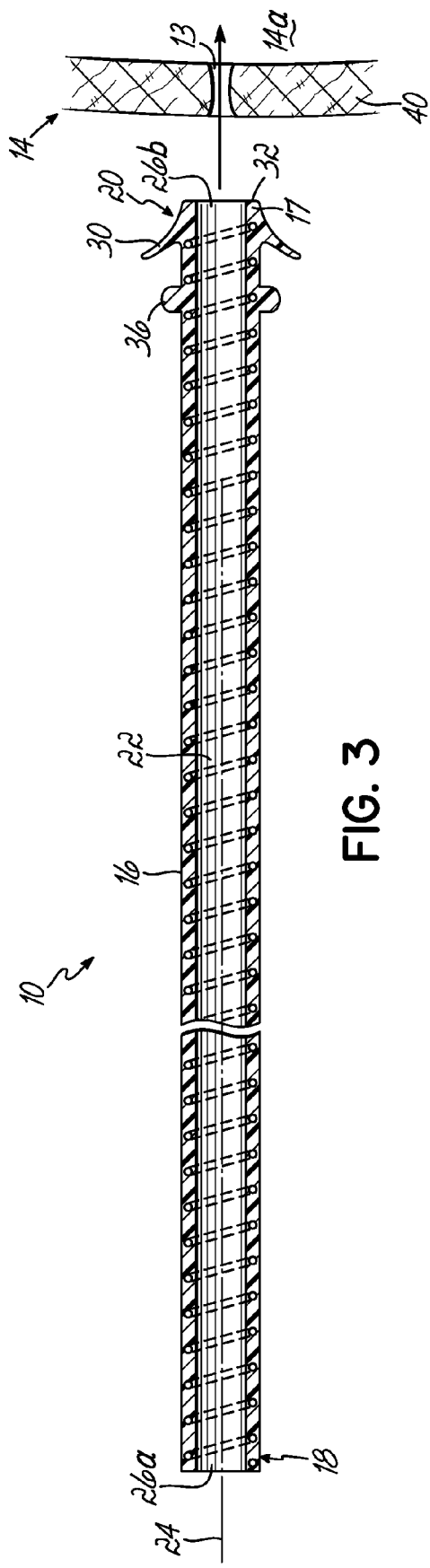
FIG. 3 is an elevational cross-sectional view of an embodiment of a cannula.

With reference to FIG. 3, the cannula 10 includes an elongate body 16 having longitudinally opposed first and second ends 18, 20 and a lumen 22 extending about a longitudinal axis 24 of the elongate body 16. The first and second ends 18, 20 define openings 26a, 26b into the lumen 22, such that blood may flow along the lumen 22 between the first and second ends 18, 20.

In one aspect of this embodiment, some or all of the elongate body 16 of the cannula 10 is made of a biocompatible yet flexible or semi-flexible material such as, and without limitation, silicone or reinforced silicone. Semi-flexible materials may be desirable, for example, where the elongate body 16 includes no rigid components e.g., metals, such that the second end 20 may remain open and thereby available for unrestricted flow of blood therethrough.

The cannula 10 includes a flared tip portion 30 disposed about the elongate body 16 to facilitate insertion of the cannula 10 into the chamber 14a of the heart 14. The flared tip portion 30 extends from the second end 20 of the elongate body 16 of the cannula 10 in a direction toward the first end 18 and flares radially outward from the longitudinal axis 24 and in such direction.

In the exemplary embodiment of FIG. 3, the flared tip portion 30 further extends from a flat portion 32 of the second end 20. Alternatively, however, the flared tip portion 30 may extend from other non-flat portions of the elongate body 16. Similarly, while the embodiment of FIG. 3 depicts the flared tip portion 30 extending from a flat portion 32 that is generally perpendicular or normal to the longitudinal axis 24, it is contemplated that the flared tip portion 30 may alternatively extend from a flat portion that is not generally perpendicular or normal to the longitudinal axis 24. For example, and without limitation, the flared tip portion 30 may extend from a flat portion that defines an acute or obtuse included angle with the longitudinal axis 24.

A flat portion, as described herein, may further be part of a wall 17 of the elongate body 16, as is the case with the exemplary flat portion 32 of FIG. 3, or alternatively be part of any other portion of the second end 20 of the elongate body 16 of the cannula 10. Likewise, the flat portion may be defined by any plane defined by the opening 26b on the second end 20 of the elongate body 16.

The flared tip portion 30 flares radially outward from longitudinal axis 24 and in a direction toward the first end 18. In the illustrative embodiment of FIG. 3, the flared tip portion 30 further flares out radially from the flat portion 32 of the second end 20 although the flared tip portion 30 may alternatively flare out radially from other non-flat portions thereof or from any alternative flat portions as generally described above.

With continued reference to FIG. 3, a ring member 36 is disposed on the elongate body 16 and extends about the longitudinal axis 24. The ring member 36 is spaced from the flared tip portion 30 to provide a suitable length of the cannula 10 to be implanted in the chamber 14a of the heart 14. More particularly, once the cannula 10 is inserted in the chamber 14a, contact between the ring member 36 and a wall 40 of the heart 14 provides an implant position of the cannula 10 along the longitudinal axis 24 and relative to the wall 40 of the heart 14, thereby defining the length of the portion of cannula 10 within the chamber 14a.

In one aspect of the embodiment of FIG. 3, the construction of the flared tip portion 30 provides a smooth, non-stepped transition between the second end 20 of the elongate body 16 of the cannula 10 and the ring member 36.

Figure 4A:
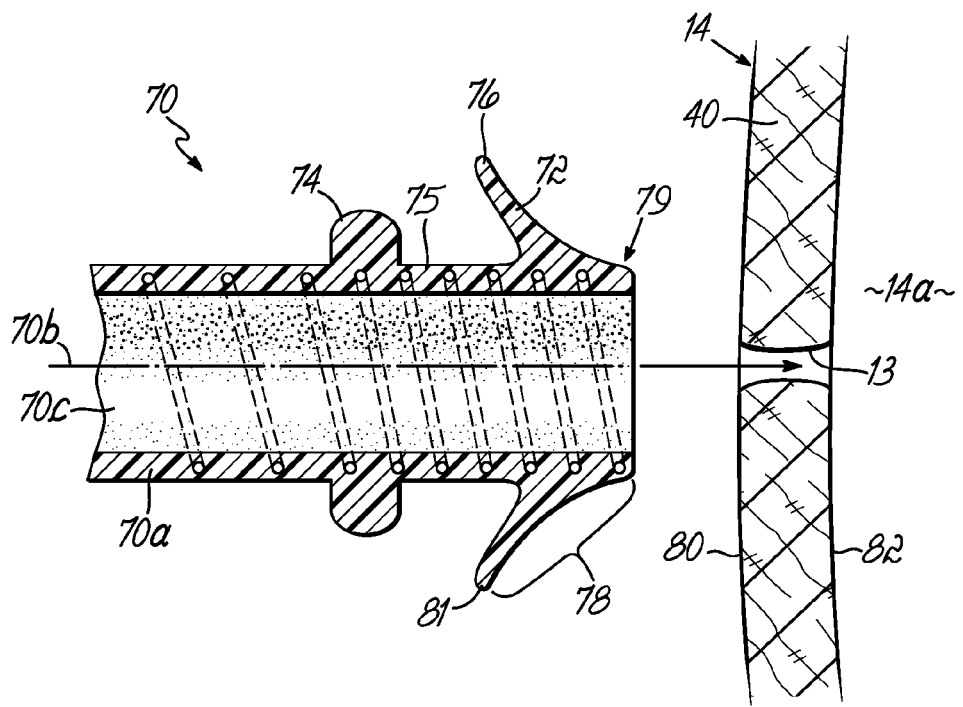
FIG. 4A is an enlarged cross-sectional view of an exemplary embodiment of a cannula prior to implantation in a human heart.

With reference to FIGS. 4A, 4B, 4C, 4D, 5A, 5B, 6A, 6B, 7A and 7B, several exemplary embodiments applying one or more of the principles described with reference to the general embodiment of FIG. 3 are shown and will be described in turn. With reference to FIGS. 4A-4D, in which like reference numerals refer to like features in FIG. 3, an exemplary embodiment of a cannula 70 includes a flexible flared tip portion 72, a ring member 74, and a gap 75 therebetween. The flexible flared tip portion 72 is defined by a wall 76 including a barbed surface 78 and extends from a second end 79 of the cannula 70 to end at an edge or surface 81. In an open position, as depicted in FIG. 4A, the edge or surface 81 is a generally annular structure that is larger in diameter than the elongate body 70a of the cannula 70 and larger as well, in diameter, than the gap 75.

With continued reference to FIGS. 4A-4D, the flexible flared tip portion 72 is adapted to flex toward the longitudinal axis 70b as the cannula 70 and, more particularly, the flexible flared tip portion 72, travels through the aperture 13 into the chamber 14a. To that end, the flexible flared tip portion 72 is made of a biocompatible flexible, resilient material such as, and without limitation, silicone. Moreover, in the exemplary embodiment of FIGS. 4A-4D, flexibility of the flexible flared tip portion 72 is facilitated by including a wall 76 of varying thickness. More specifically, the thickness of the wall 76 is greater in regions near the second end 79 than in regions proximate the edge or surface 81.

Alternatively, flexibility of the flexible flared tip portion 72 can be controlled or influenced in other ways. For example, and without limitation, the flexible flared tip portion 72 may include flexible polymer structures, flexible metallic structures such as NiTi, rigid structures such as structures formed with titanium or titanium alloys, or struts (not shown).

With continued reference to FIGS. 4A-4D, the cannula 70 further includes a ring member 74 spaced from the flexible flared tip portion 72. The ring member 74 is made of a resilient material to facilitate travel thereof through the aperture 13 into or out of the chamber 14a. To this end, the ring member 74 may include, without limitation, flexible, resilient, biocompatible materials such as silicone.

Figure 4B:
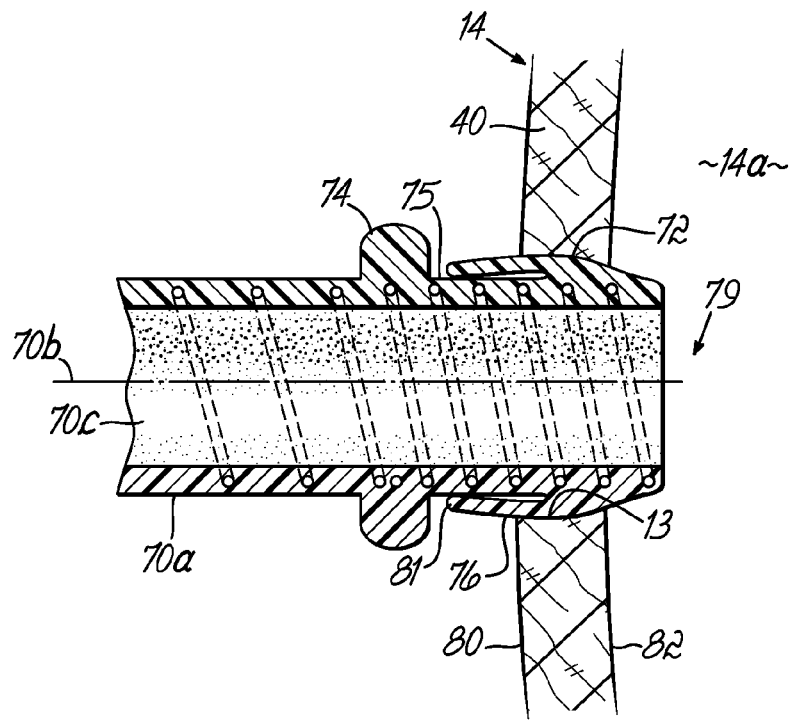
FIG. 4B is an enlarged cross-sectional view of the cannula of FIG. 4A in a subsequent step during implantation thereof.

As explained above, the cannula 70 is designed to be implanted in a chamber 14a of the heart 14. To that end, the exemplary cannula 70 is inserted through the aperture 13 in the wall 40 of the heart 14. During insertion, the wall 76 of the flexible flared tip portion 72 is pushed radially inward i.e., toward the longitudinal axis 70b of the cannula 70, as depicted in FIG. 4B, by portions of the wall 40 of the heart 14 around the aperture 13. The flexible flared tip portion 72 flares back to its original shape, as depicted in FIGS. 4C-4D, once the flexible flared tip portion 72 passes completely through the wall 40 and is completely received within the chamber 14a.

Figure 4C:
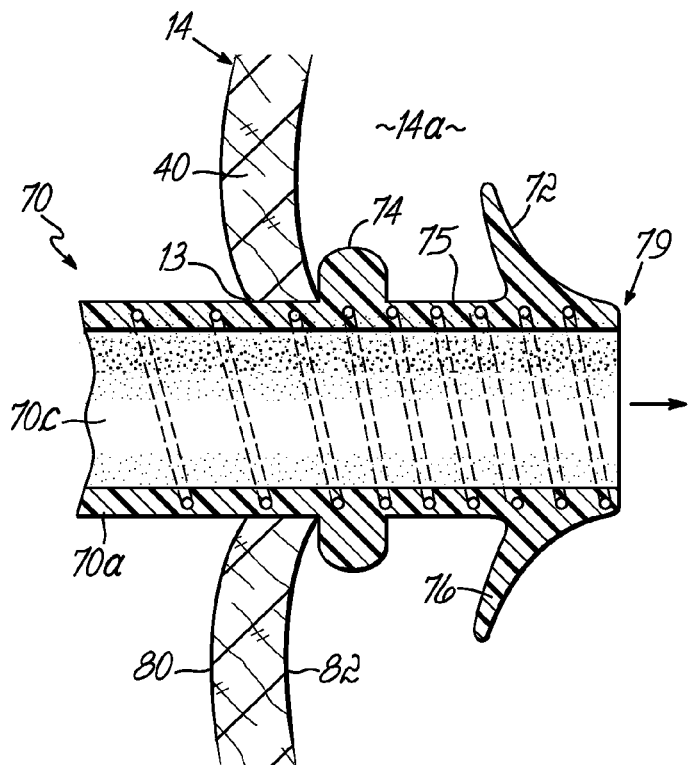
FIG. 4C is an enlarged cross-sectional view of the cannula of FIGS. 4A-4B in another subsequent step during implantation thereof.
Figure 4D:
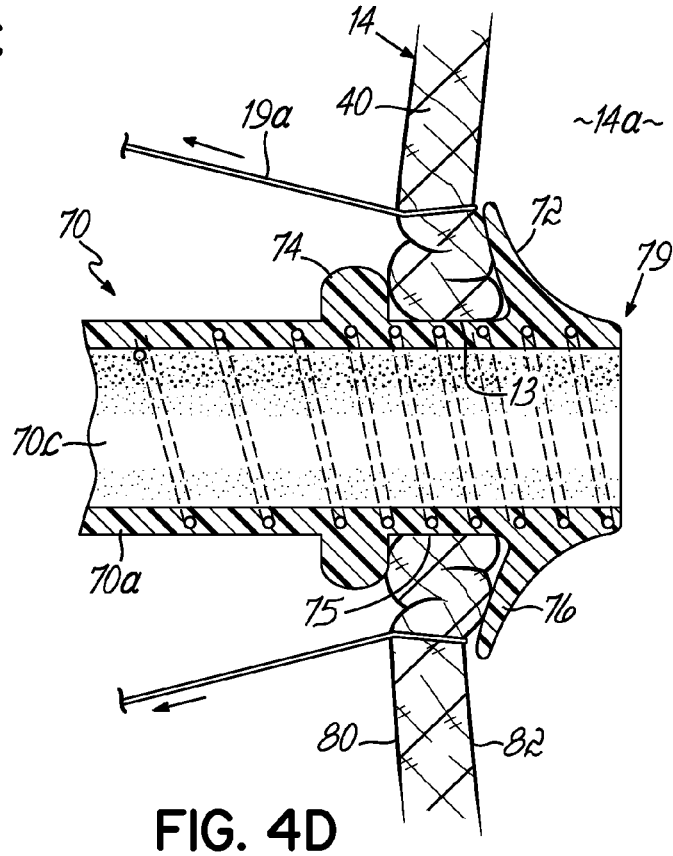
FIG. 4D is an enlarged cross-sectional view of the cannula of FIGS. 4A-4C in yet another subsequent step during implantation thereof.

With reference to FIGS. 4C-4D, implantation of the cannula 70 may include, in addition to insertion of the flexible flared tip portion 72, insertion of the ring member 74 through the aperture 13 and subsequent retrieval thereof (i.e., in an opposite direction away from the chamber 14a). Retrieval or removal of the ring member 74 may carry with it loose tissue material lying on surfaces defining the aperture 13, produced as a result of the procedure that created the aperture 13, and gathered by the previous passage of the flexible flared tip portion 72 through the aperture 13.

The final position of the cannula 70 within the chamber 14a, best appreciated in FIG. 4D, is therefore determined by contact between the ring member 74 and the outer surface 80 of the wall 40 of the heart 14. Moreover, contact between the edge or surface 81 of the flexible flared tip portion 72 and an inner surface 82 of the wall 40 further establishes the final position of the cannula 70 within the chamber 14a. In another aspect of this embodiment, the final position of the cannula 70 within the chamber 14a can be further secured, for example, and without limitation, via a purse string suture 19a applied to portions of the wall 40 surrounding the gap 75 between the flexible flared tip portion 72 and the ring member 74.

The flexible nature of the flexible flared tip portion 72 permits sealing of the aperture 13 from within the chamber 14a even in cases where the inner surface 82 surrounding the aperture 13 is uneven and/or in cases where the cannula 70 is not orthogonally oriented with respect to the inner surface 82. More particularly, the wall 76 defining the flexible flared tip portion 72 compensates for any unevenness or non-orthogonal orientation of the cannula 70 by flexing to different degrees along the circumference defined by the edge or surface 81.

In another aspect of the embodiment of FIGS. 4A-4D, overgrowth of tissue surrounding the aperture 13 into the lumen 70c of the cannula 70 is minimized. More particularly, the shape of the wall 76 of the flexible flared tip portion 72 provides a relatively long path between the aperture 13 and the second end 79 such that tissue from portions of the wall 40 defining the aperture 13 is less likely to reach the second end 79 of the cannula 70.

Figure 5A:
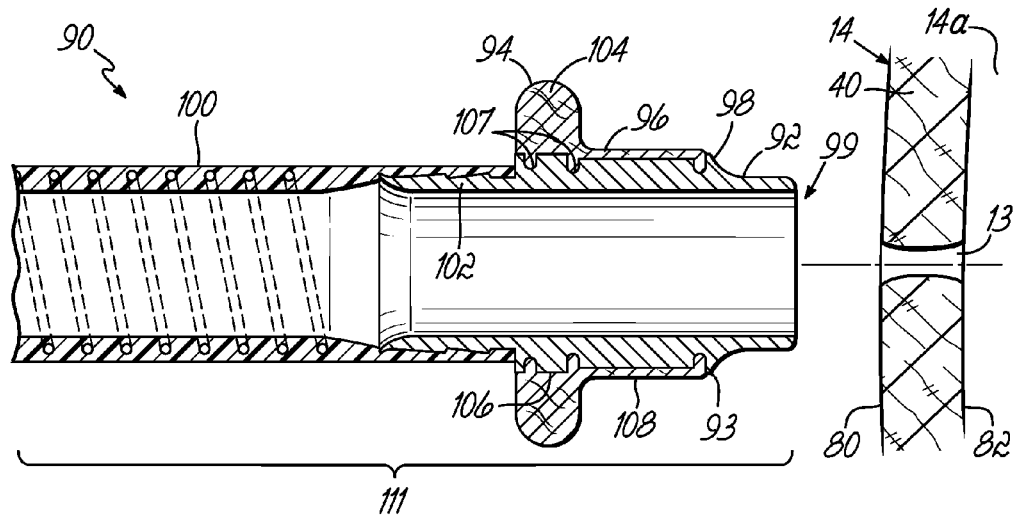
FIG. 5A is an enlarged cross-sectional view of an alternative exemplary embodiment of a cannula prior to implantation in a human heart.
Figure 5B:
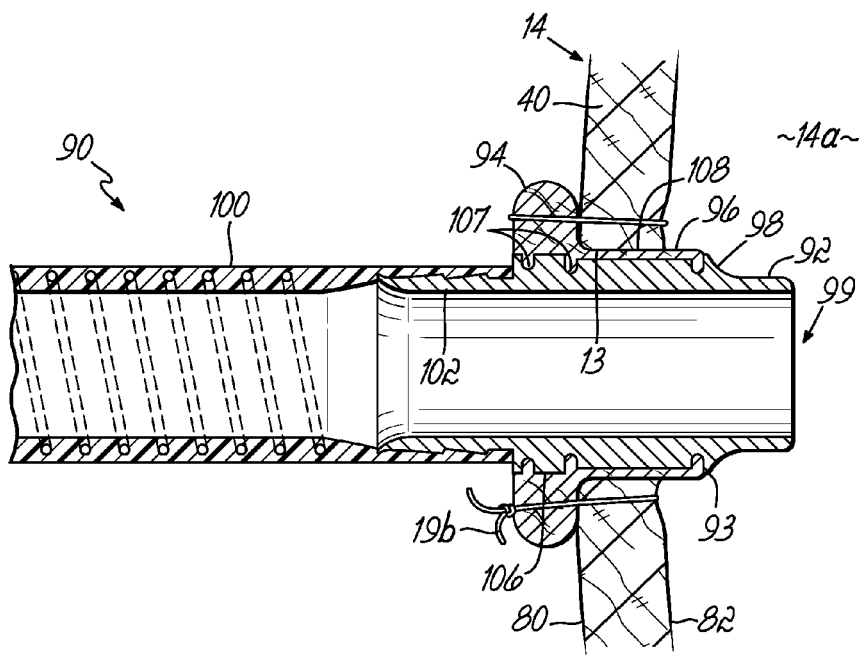
FIG. 5B is a similar view of the embodiment of FIG. 5A in a subsequent step during implantation thereof.

With reference to FIGS. 5A-5B, in which like reference numerals refer to like features in FIG. 3, an alternate embodiment of a cannula 90 includes a rigid flared tip portion 92, a ring member 94 and a gap 96 therebetween. The rigid flared tip portion 92 includes flaring walls 98 extending from the second end 99 of the cannula 90 and ending, in cross-section, at a juncture 93 with the gap 96.

In one aspect of this illustrative embodiment, the rigid flared tip portion 92 is made of a suitably chosen rigid, biocompatible material, such as, and without limitation, a suitably chosen metal. For example, and without limitation, the rigid flared tip portion 92 may be made of titanium or an alloy thereof. Similarly, the rigid flared tip portion 92, by including a non-porous surface, prevents or minimizes overgrowth of tissue thereon, thereby avoiding or minimizing restriction to the flow of blood through the second end 99.

The rigid flared tip portion 92 is suitably coupled to a main portion 100 of the cannula 90 to thereby define an elongate body 111 thereof. To this end, coupling components are suitably chosen and may include, without limitation, adhesives, mechanical fasteners, fittings, integral formation, and the like. In the exemplary embodiment of FIGS. 5A-5B, the rigid flared tip portion 92 includes a cylindrical portion 102 embedded within a segment of the main portion 100 of the elongate body 111 of the cannula 90.

The ring member 94 is disposed around the elongate body 111 and is spaced from the rigid flared tip portion 92. In addition to establishing a final position of the cannula 90 within the chamber 14a, the ring member 94 permits coupling of the cannula 90 to the wall 40 of the heart 14. To this end, the ring member 94 includes a fabric 104 adapted to be surgically sutured to the wall 40 The fabric 104 may alternatively or additionally be adapted for tissue ingrowth therethrough, thereby permitting locking engagement of the ring member 94 with tissue positioned proximate ring member 94. For example, and without limitation, the ring member 94 may include a polyester-based fabric, such as one commercially available under the tradename Dacron®, covering a structural portion 106 of the ring member 94.

With continued reference to FIGS. 5A-5B, the fabric 104 may be coupled to the structural portion 106 of the ring member 94 by any suitably chosen components and/or methods. For example, the fabric 104 may be adhesively bonded to an outer surface of the structural portion 106 of the ring member 94. Alternatively, the fabric 104 may be attached via grooves 107 or the like on the outer surface of the structural portion 106 and corresponding ties (not shown) extending from the fabric 104.

Persons of ordinary skill in the art will appreciate that, although the exemplary embodiment herein described includes a fabric 104 substantially defining a volume of the ring member 94, the ring member 94 may alternatively include other rigid or semi-rigid substructures (not shown) at least partially defining the volume of ring member 94 and covered by fabric 104.

As mentioned above, the cannula 90 includes a gap 96 disposed between the rigid flared tip portion 92 and the ring member 94. In the exemplary embodiment of FIGS. 5A-5B, the gap 96 includes a fabric 108 similar in structure, composition, coupling to an underlying surface, and function, to the fabric 104 of the ring member 94, such that the fabric 108 provides a suturing surface to which portions of the heart 14, such as wall 40, can be coupled. Moreover, the fabric 108 may alternatively or additionally provide a surface into which tissue of the wall 40 of the heart 14 can grow, further securing the position of the implanted cannula 90 within the chamber 14a.

Similarly to the procedure described in regard to the embodiments of FIGS. 4A-4D, the cannula 90 is inserted through the aperture 13 in the wall 40 of the heart 14 to establish fluid communication with the chamber 14a. To this end, the cannula 90 may be inserted until the ring member 94 contacts the outer surface 80 of the wall 40, thereby establishing a final position for the cannula 90 within the chamber 14a.

Once the final position of the cannula 90 is reached i.e., by contact between the ring member 94 and the wall 40, the cannula 90 may be secured by any conventional methods and/or components known to those of ordinary skill in the art. Thus, the cannula 90 can be coupled to the wall 40 of the heart 14, for example, via conventional stitches 19b (FIG. 5B) engaging either or both of the fabrics 104, 108, respectively, of the ring member 94 and gap 96.

Figure 6A:
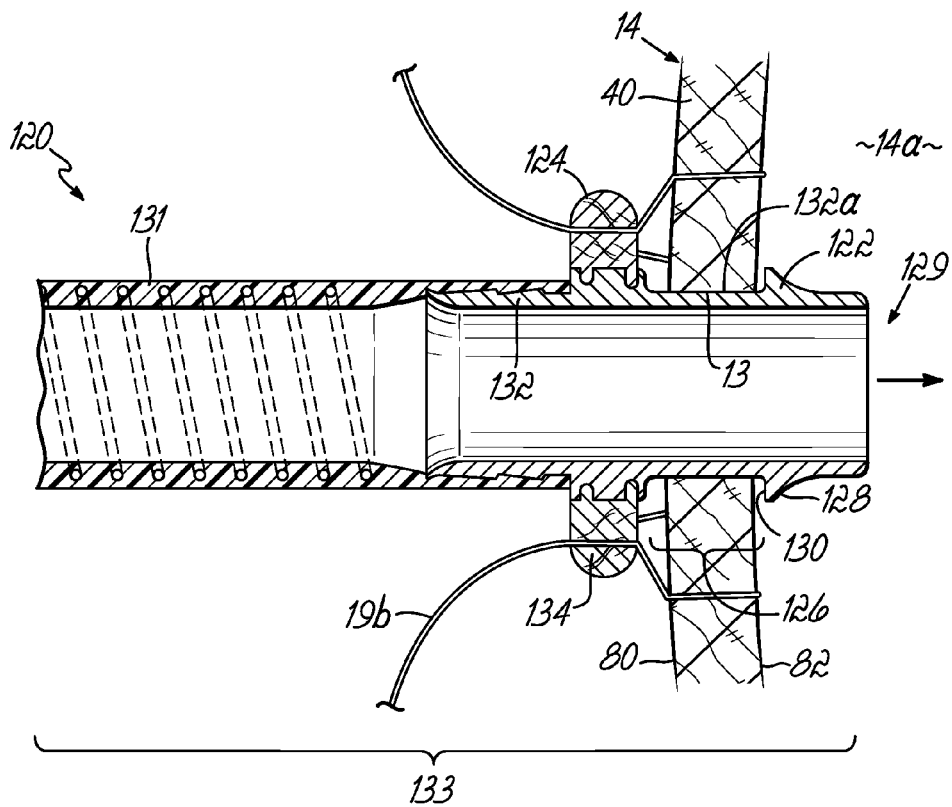
FIG. 6A is an enlarged cross-sectional view of an alternative exemplary embodiment of a cannula during implantation in a human heart.
Figure 6B:
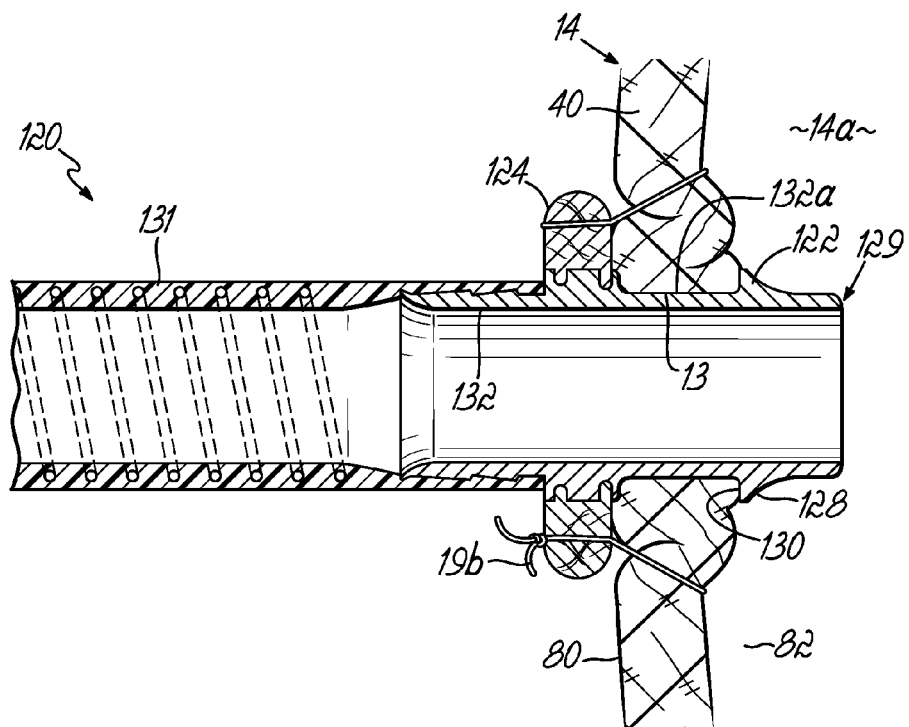
FIG. 6B is an enlarged cross-sectional view of the cannula of FIG. 6A in a subsequent step during implantation thereof.

With reference to FIGS. 6A-6B, in which like reference numerals refer to like features in FIG. 3, an alternate exemplary embodiment of a cannula 120 includes a barbed flared tip portion 122, a ring member 124 and a gap 126 therebetween. The barbed flared tip portion 122 includes flaring walls 128 extending from the second end 129 of the cannula 120 and ending at a surface 130 defining a juncture with the gap 126 and extending around an outer surface 132a of the elongate body 133 of the cannula 120.

Similarly to the embodiment of the cannula 90 (FIGS. 5A-5B), the barbed flared tip portion 122 is made of a suitably chosen rigid, biocompatible material, such as, and without limitation, titanium or an alloy thereof. Similarly, the barbed flared tip portion 122, by including a non-porous surface, prevents or minimizes overgrowth of tissue thereon, thereby avoiding or minimizing restriction to the flow of blood through the second end 129.

The barbed flared tip portion 122 is suitably coupled to a main portion 131 of the cannula 120 to thereby define the elongate body 133 thereof. To this end, coupling components are suitably chosen and may include, without limitation, adhesives, mechanical fasteners, fittings, integral formation, and the like. In the exemplary embodiment of FIGS. 6A-6B, the barbed flared tip portion 122 includes a cylindrical portion 132 embedded within a segment of the main portion 131 of the elongate body 133.

The ring member 124 is disposed around the elongate body 133 and is spaced from the barbed flared tip portion 122. Similarly to the embodiment of the cannula 90 (FIGS. 5A-5B), in addition to establishing a final position of the cannula 120 within the chamber 14*a*, the ring member 124 permits coupling of the cannula 120 to the wall 40 of the heart 14. To this end, the ring member 124 includes a fabric 134 adapted to be surgically sutured to the wall 40 The fabric 134 may alternatively or additionally be adapted for tissue ingrowth therethrough, thereby permitting locking engagement of the ring member 124 with tissue positioned proximate ring member 124. For example, and without limitation, the ring member 124 may include a polyester-based fabric, such as one commercially available under the tradename Dacron®, covering a structural portion 136 of the ring member 124.

In this exemplary embodiment, the fabric 134 is coupled to the structural portion 136 of the ring member 124 by any suitably chosen components and/or methods. For example, the fabric 134 may be adhesively bonded to an outer surface of the structural portion 136 of the ring member 124. Alternatively, the fabric 134 may be attached via grooves 137 or the like on the outer surface of the structural portion 136 and corresponding ties (not shown) extending from the fabric 134.

Persons of ordinary skill in the art will appreciate that, although the exemplary embodiment herein described includes a fabric 134 substantially defining a volume of the ring member 124, the ring member 124 may alternatively include other rigid or semi-rigid substructures (not shown) at least partially defining the volume of ring member 124 and covered by fabric 134.

Similarly to the procedure described in regard to the embodiments of FIGS. 4A-4B and 5A-5B, the cannula 120 of FIGS. 6A-6B is inserted through the aperture 13 in the wall 40 of the heart 14 to establish fluid communication with the chamber 14*a*. To this end, the cannula 120 may be inserted until the ring member 124 contacts the outer surface 80 of the wall 40, thereby establishing a final position for the cannula 120 within the chamber 14*a*. Moreover, the surface 130 provides sealing of the aperture 13 from within the chamber 14*a* by being positioned against the inner surface 82 of the wall 40.

With continued reference to FIGS. 6A-6B, once the final position of the cannula 120 is reached i.e., by contact between the ring member 124 and wall 40, the cannula 120 may be secured by any conventional methods and/or components known to those of ordinary skill in the art. Thus, the cannula 120 can be coupled to the wall 40 of the heart 14, for example, via conventional stitches 19*b* engaging the fabric 134 of the ring member 124.

Figure 7A:
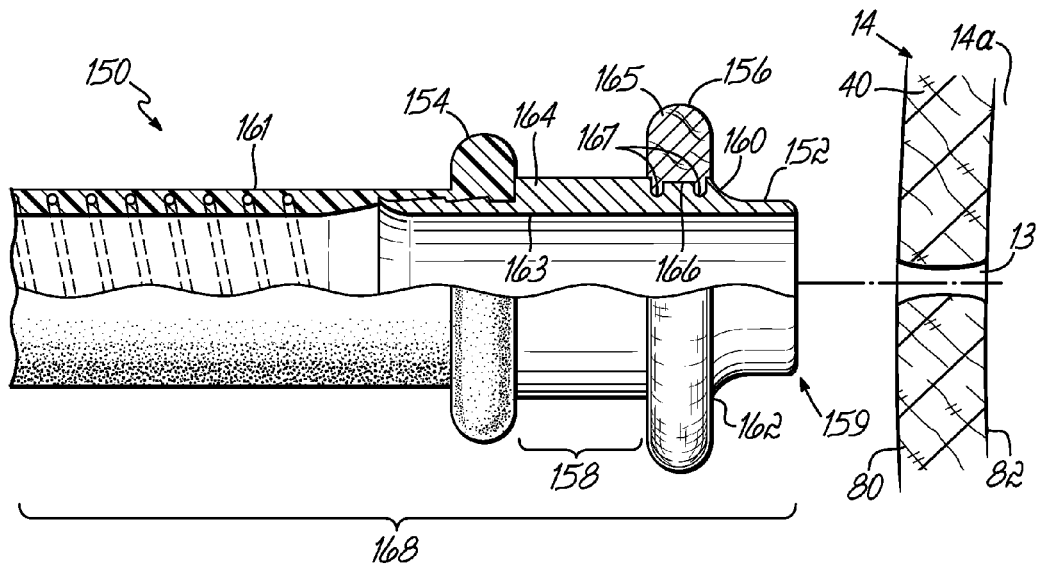
FIG. 7A is an enlarged partial cross-sectional view of another alternative exemplary embodiment of a cannula prior to implantation in a human heart.
Figure 7B:
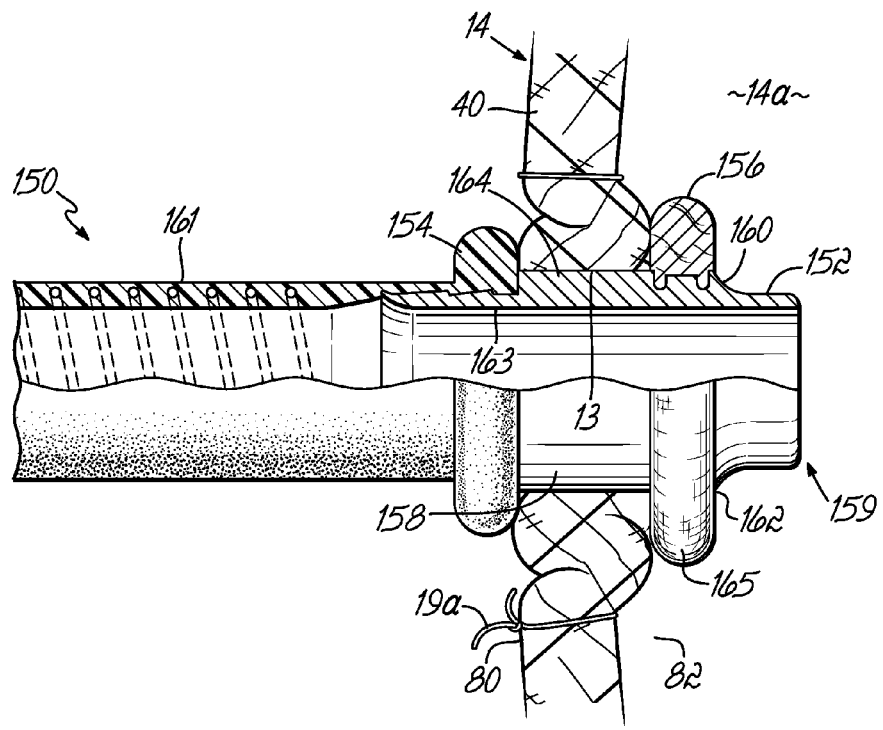
FIG. 7B is a similar view of the embodiment of FIG. 7A in a subsequent step during implantation thereof.

With reference to FIGS. 7A-7B, in which like reference numerals refer to like features in FIG. 3, an alternate exemplary embodiment of a cannula 150 includes a rigid flared tip portion 152, a first ring member 154 spaced from the rigid flared tip portion 152, a second ring member 156 adjacent the rigid flared tip portion 152, and a gap 158 between the first and second ring members 154, 156.

The rigid flared tip portion 152 includes flaring walls 160 extending from the second end 159 of the cannula 150 and ending at a juncture 162 with a tubular section 164 of the elongate body 168. In this exemplary embodiment, the rigid flared tip portion 152 and the tubular section 164 have the same diameter at the juncture 162. Persons of ordinary skill in the art will, however, readily appreciate that the respective diameters of the rigid flared tip portion 152 and tubular section 164 at the juncture 162 may, alternatively, differ with respect to one another.

In one aspect of this illustrative embodiment, the rigid flared tip portion 152 is made of a suitably chosen rigid, biocompatible material, such as, and without limitation, a suitably chosen metal. For example, and without limitation, the rigid flared tip portion 152 may be made of titanium or an alloy thereof. Similarly, the rigid flared tip portion 152, by including a non-porous surface, prevents or minimizes overgrowth of tissue thereon, thereby avoiding or minimizing restriction to the flow of blood through the second end 159.

The rigid flared tip portion 152 is suitably coupled to a main portion 161 of the cannula 150 to thereby define the elongate body 168 thereof. To this end, coupling components are suitably chosen and may include, without limitation, adhesives, mechanical fasteners, fittings, integral formation, and the like. In the exemplary embodiment of FIGS. 7A-7B, the rigid flared tip portion 152 includes a cylindrical portion 163 embedded within a segment of the main portion 161 of the elongate body 168 of the cannula 150.

With continued reference to FIGS. 7A-7B, the cannula 150 includes a first ring member 154 spaced from the rigid flared tip portion 152. The first ring member 154 is made of a resilient material so as to facilitate travel thereof into or out of the chamber 14*a*. To this end, the first ring member 154 may include, without limitation, flexible, resilient, biocompatible materials such as silicone.

As mentioned above, the cannula 150 includes a second ring member 156. The second ring member 156 is disposed around the tubular section 164 of the elongate body 168 and lies adjacent the rigid flared tip portion 152. The second ring member 156 permits coupling of the cannula 150 to the inner surface 82 of the wall 40 of the heart 14. To this end, the second ring member 156 includes a fabric 165 adapted to be surgically sutured to the wall 40. The fabric 165 may alternatively or additionally be adapted for tissue ingrowth therethrough, thereby permitting locking engagement of the ring member 156 with tissue positioned proximate ring member 156. For example, and without limitation, the second ring member 156 may include a polyester-based fabric, such as one commercially available under the tradename Dacron®, covering a structural portion 166 of the second ring member 156.

Moreover, the porous structure of the second ring member 156, which is provided by the fabric 165, may alternatively or additionally provide a surface into which tissue within the chamber 14*a* of the heart 14 can grow, thereby providing long-term fixation of the cannula 150 in the chamber 14*a*. In another aspect of this embodiment, by permitting tissue ingrowth, the second ring member 156 further seals the aperture 13 in the wall 40 of the heart 14.

In the exemplary embodiment of FIGS. 7A-7B, the fabric 165 is coupled to the structural portion 166 of the second ring member 156 by any suitably chosen components and/or methods. For example, the fabric 165 may be adhesively bonded to an outer surface of the structural portion 166 of the second ring member 156. Alternatively, the fabric 165 may be attached via grooves 167 or the like on the outer surface of the structural portion 166 and corresponding ties (not shown) extending from the fabric 165.

Persons of ordinary skill in the art will appreciate that, although the exemplary embodiment herein described includes a fabric 165 substantially defining a volume of the second ring member 156, the second ring member 156 may alternatively include other rigid or semi-rigid substructures (not shown) at least partially defining the volume of second ring member 156 and covered by fabric 165.

Similarly to the procedure described in regard to the embodiments of FIGS. 4A-4D, 5A-5B, and 6A-6B, the cannula 150 of FIGS. 7A-7B is inserted through the aperture 13 in the wall 40 of the heart 14 to establish fluid communication with the chamber 14a. To this end, the cannula 150 may be inserted until the first and second ring members 154, 156 complete passage through the aperture 13 and lie within the chamber 14a.

With continued reference to FIGS. 7A-7B, implantation of the cannula 150 within the chamber 14a may include, in addition to movement of the cannula 150 in a first direction toward the heart 14 and subsequent insertion of the rigid flared tip portion 152 and first and second ring members 154, 156 into the chamber 14a, subsequent removal of the first ring member 154 from the chamber 14a (i.e., in a second direction opposite the first direction). Retrieval of the first ring member 154 drags therewith loose tissue material lying on surfaces defining the aperture 13, and produced as a result of the procedure that previously produced the aperture 13.

The final position of the cannula 150 within the chamber 14a is therefore established by contact between the first ring member 154 and the outer surface 80 of the wall 40 of the heart 14. Moreover, contact between the second ring member 156 and the inner surface 82 of the wall 40 further establishes the final position of the cannula 150 within the chamber 14a. In another aspect of this embodiment, the final position of the cannula 150 within the chamber 14a can be further secured, for example, and without limitation, via a purse string suture 19a (FIG. 7B) applied to portions of the wall 40 of the heart 14 surrounding the gap 158 between the first and second ring members 154, 156.

While the exemplary embodiments of FIGS. 4A-4B, 5A-5B, 6A-6B, and 7A-7B have been described as outlined above, it is contemplated that any of the exemplary cannulae 70, 90, 120, 150 may incorporate aspects described in regard to any of the other embodiments described herein. For example, and without limitation, either of the cannulae 70, 90, 120 (respectively FIGS. 4A-4D, 5A-5B, and 6A-6B) may further include a second ring member similar to the second ring member 156 of the exemplary cannula 150 of FIGS. 7A-7B.

Similarly, while the above exemplary embodiments depict generally round ring members, persons of ordinary skill in the art will readily appreciate that any of the ring members can take on any other suitably chosen shape. A ring member of any embodiment may hence take on any regular or irregular shape, so long as the chosen shape is configured to permit the ring member or members of an embodiment to carry out the functions described above.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A method of implanting a cannula having a longitudinal axis into a chamber of a heart of a patient having a circulatory system, the chamber of the heart having a wall and an aperture through the wall, the method comprising:
    moving the cannula in a first direction through the aperture such that a lumen of the cannula communicates with the chamber for drawing blood from the chamber into the lumen;
    receiving a rigid flared tip portion of the cannula within the chamber of the heart, the rigid flared tip portion extending from a flat portion on an end of the cannula residing in the chamber and flaring radially outward relative to the longitudinal axis and in a direction away from the end;
    establishing an implant position of the cannula within the chamber of the heart and along the longitudinal axis by contacting the wall of the chamber of the heart with a ring member fixedly connected with the cannula and extending around the longitudinal axis, the ring member spaced at a fixed distance from the rigid flared tip portion such that the wall is positioned in a gap defined between the ring member and the rigid flared tip portion, the cannula including a fabric positioned in the gap, wherein receiving the rigid flared tip portion within the chamber of the heart includes receiving the fabric within the aperture in the wall of the chamber, the fabric being configured to facilitate tissue ingrowth from the aperture to the fabric positioned in the gap;
    coupling the gap to the wall of the chamber of the heart, including suturing the fabric to the wall of the chamber; and
    guiding blood through the lumen between the chamber of the heart and a separate location in the circulatory system of the patient while the cannula remains fixed in the implant position.

2. The method of claim 1, wherein moving the cannula in the first direction further includes inserting the ring member into the chamber, and the method further comprises moving the cannula in a second direction opposite the first direction until the ring member contacts an outer surface on the wall of the chamber of the heart.

3. The method of claim 2, wherein moving the cannula in the second direction opposite the first direction further comprises contacting a second ring member with an inner surface of the wall of the chamber of the heart.

4. The method of claim 1, further comprising coupling the ring member to the wall of the chamber of the heart.

5. The method of claim 4, wherein coupling the ring member further comprises suturing the ring member to the wall of the chamber of the heart.

6. The method of claim 1, further comprising interlocking the ring member with tissue positioned proximate the ring member.

7. The method of claim 1, further comprising:
    contacting an inner surface of the wall of the chamber with a fabric ring member.

8. The method of claim 1, wherein receiving the rigid flared tip portion of the cannula within the chamber includes receiving a rigid flared tip portion having a flaring wall defining a varying thickness along a length of the flaring wall.

9. The method of claim 1, wherein receiving the rigid flared tip portion of the cannula within the chamber includes receiving a metallic flared tip portion.

10. The method of claim 1, wherein receiving a rigid flared tip portion of the cannula within the chamber includes receiving a barbed flared tip portion.

11. A method of implanting a cannula having a longitudinal axis into a chamber of a heart, the chamber of the heart having a wall and an aperture through the wall, the method comprising:

moving the cannula in a first direction through the aperture such that a lumen of the cannula communicates with the chamber for drawing blood from the chamber into the lumen;

flexing a flared tip portion of the cannula radially inwardly toward the longitudinal axis while moving the cannula in the first direction and inserting the flared tip portion through the aperture, the flared tip portion extending from a flat portion on an end of the cannula residing in the chamber and flaring radially outward relative to the longitudinal axis and in a direction away from the end; and establishing a position of the cannula within the chamber of the heart and along the longitudinal axis by contacting the wall of the chamber of the heart with a ring member connected with the cannula and extending around the longitudinal axis, the ring member spaced from the flared tip portion such that the wall is positioned in a space between the ring member and the flared tip portion.

\* \* \* \* \*